(12) United States Patent
Shay

(10) Patent No.: US 8,501,984 B2
(45) Date of Patent: Aug. 6, 2013

(54) PREPARATION OF PALLADIUM-GOLD CATALYST

(75) Inventor: Daniel Travis Shay, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 13/571,848

(22) Filed: Aug. 10, 2012

(65) Prior Publication Data

US 2012/0302784 A1  Nov. 29, 2012

Related U.S. Application Data

(62) Division of application No. 12/653,592, filed on Dec. 16, 2009, now Pat. No. 8,273,682.

(51) Int. Cl.
*C07C 67/02* (2006.01)
*B01J 23/00* (2006.01)
*B01J 21/00* (2006.01)
*B01J 20/00* (2006.01)

(52) U.S. Cl.
USPC ........... 560/261; 502/330; 502/339; 502/350; 502/439

(58) Field of Classification Search
USPC .......... 562/261; 502/330, 339, 350, 439
See application file for complete search history.

(56) References Cited

U.S. PATENT DOCUMENTS

| | | | |
|---|---|---|---|
| 4,992,406 A | 2/1991 | Mauldin et al. | |
| 5,140,050 A | 8/1992 | Mauldin et al. | |
| 5,783,726 A * | 7/1998 | Lemanski et al. | 560/261 |
| 5,804,296 A * | 9/1998 | Itoh et al. | 428/326 |
| 5,859,287 A * | 1/1999 | Nicolau et al. | 560/241 |
| 5,977,012 A | 11/1999 | Kharas et al. | |
| 6,040,474 A * | 3/2000 | Jobson et al. | 560/243 |
| 6,107,514 A * | 8/2000 | Nicolau et al. | 560/245 |
| 6,114,574 A * | 9/2000 | Sen et al. | 562/410 |
| 6,180,821 B1 * | 1/2001 | Jobson et al. | 560/243 |
| 6,225,496 B1 * | 5/2001 | Baker et al. | 560/245 |
| 6,274,531 B1 * | 8/2001 | Nicolau et al. | 502/243 |
| 6,696,596 B1 * | 2/2004 | Herzog et al. | 560/245 |
| 6,797,669 B2 * | 9/2004 | Zhang et al. | 502/339 |
| 6,803,340 B2 * | 10/2004 | Lee et al. | 502/309 |
| 6,849,243 B1 | 2/2005 | Hagemeyer et al. | |
| 6,987,200 B2 * | 1/2006 | Hagemeyer et al. | 560/261 |
| 6,992,040 B2 * | 1/2006 | Muller et al. | 502/327 |
| 7,387,981 B1 * | 6/2008 | Kaminsky et al. | 502/243 |
| 7,491,843 B2 * | 2/2009 | Jobson et al. | 560/241 |
| 7,514,476 B2 * | 4/2009 | Parasher et al. | 516/78 |
| 7,521,393 B2 * | 4/2009 | Blankenship et al. | 502/330 |
| 7,612,244 B2 * | 11/2009 | Strebelle et al. | 570/244 |
| 7,638,459 B2 * | 12/2009 | Rende et al. | 502/300 |
| 7,674,744 B2 * | 3/2010 | Shiratori et al. | 502/327 |
| 7,745,370 B2 * | 6/2010 | Blankenship et al. | 502/262 |
| 7,820,853 B2 * | 10/2010 | Johnston et al. | 560/261 |
| 7,842,641 B2 * | 11/2010 | Fu et al. | 502/242 |
| 8,178,715 B2 * | 5/2012 | Johnston et al. | 560/261 |
| 8,273,682 B2 | 9/2012 | Shay | |
| 8,329,611 B2 | 12/2012 | Shay | |
| 2001/0056201 A1 * | 12/2001 | Couves et al. | 560/245 |
| 2002/0025905 A1 | 2/2002 | Harris et al. | |
| 2002/0028966 A1 * | 3/2002 | Blum et al. | 560/261 |
| 2002/0062039 A1 * | 5/2002 | Salem et al. | 560/261 |
| 2005/0095189 A1 | 5/2005 | Brey et al. | |
| 2005/0261125 A1 | 11/2005 | Sagae | |
| 2008/0153692 A1 * | 6/2008 | Kimmich et al. | 502/242 |
| 2008/0287289 A1 * | 11/2008 | Wang et al. | 502/170 |
| 2009/0093653 A1 * | 4/2009 | Mayer et al. | 560/261 |
| 2010/0099552 A1 * | 4/2010 | Fu et al. | 502/209 |
| 2010/0168466 A1 * | 7/2010 | Johnston et al. | 560/261 |
| 2011/0087047 A1 * | 4/2011 | Hallinan et al. | 560/261 |

FOREIGN PATENT DOCUMENTS

| | | |
|---|---|---|
| EP | 516262 A1 | 12/1992 |
| WO | 2011075278 A1 | 6/2011 |

OTHER PUBLICATIONS

Aida Guitierrez-Alejandre, A Vibrational and Spectroscopic Study, WO3/TiO2-A1s03 of Catalyst Precursors, Langmuir, vol. 14, No. 3, 1998, pp. 630-639.

Mu, X., The Preparation of Pd/SiO2 Catalyst by Chemical Vapor Deposition in a Fluidized-Bed Reactor, Applied Catalysis A: General 248 (2003), pp. 85-95.

* cited by examiner

*Primary Examiner* — Cam N. Nguyen

(57) ABSTRACT

A method for preparing a palladium-gold catalyst containing a titania extrudate is disclosed. The titania extrudate is produced by using a carboxyalkyl cellulose and a hydroxyalkyl cellulose as extrusion aids. The titania extrudate has improved processibility and/or mechanical properties. After calcination, the extrudate is used as a carrier for the palladium-gold catalyst. The catalyst is useful in producing vinyl acetate by oxidizing ethylene with oxygen in the presence of acetic acid.

5 Claims, No Drawings

PREPARATION OF PALLADIUM-GOLD CATALYST

This application is a divisional of application Ser. No. 12/653,592, filed Dec. 16, 2009, which is U.S. Pat. No. 8,273,682, issued Sep. 25, 2012.

FIELD OF THE INVENTION

The invention relates to a method of preparing a palladium-gold catalyst containing a titania extrudate.

BACKGROUND OF THE INVENTION

Palladium-gold catalysts are useful in the oxidation of ethylene or propylene in the presence of acetic acid to produce vinyl acetate or allyl acetate. Acetoxylation is commonly conducted in the vapor phase using a supported palladium-gold catalyst. Palladium-gold catalysts containing titania carriers are known (U.S. Pat. No. 6,022,823; U.S. Pat. Appl. Pub. Nos. 2008/0146721 and 2008/0281122; co-pending application Ser. No. 11/801,935 filed May 11, 2007). Acetoxylation is is preferably conducted in a fixed-bed reactor.

Commercially, titania is produced as a fine powder. To prepare catalysts suitable for fixed-bed reactions, it is necessary to form titania powder into particles, such as spheres, tablets, extrudates, and the like. Despite many efforts in developing methods for producing titania extrudates in the past, many are not suitable for commercial production because of their poor processibility. Therefore, there is a continued need to develop new processes for making titania extrudates that can be used as carriers for palladium-gold catalysts (see, e.g., co-pending application Ser. No. 12/653,563 filed on Dec. 16, 2009).

SUMMARY OF THE INVENTION

The invention is a method for preparing a palladium-gold catalyst. The method comprises (a) mixing titania, a carboxyalkyl cellulose, and a hydroxyalkyl cellulose to form a dough; (b) extruding the dough to produce an extrudate; (c) calcining the extrudate to produce a calcined extrudate; (d) impregnating the calcined extrudate with a palladium compound and a gold compound to produce an impregnated extrudate; and (e) calcining the impregnated extrudate to produce the palladium-gold catalyst. The invention also includes a process for producing vinyl acetate comprising reacting ethylene, oxygen, and acetic acid in the presence of a palladium-gold catalyst.

DETAILED DESCRIPTION OF THE INVENTION

The invention is a method for preparing a palladium-gold catalyst containing a titania carrier. The method comprises mixing titania, a carboxyalkyl cellulose, and a hydroxyalkyl cellulose to form a dough. Suitable titanias can be rutile, anatase, brookite, or a mixture of them. Preferably the titania is an anatase. Titanias may be produced by the chloride process, the sulfate process, the hydrothermal process, or the flame hydrolysis of titanium tetrachloride. Examples of suitable titanias include TiONA® DT-51, DT-52, DT-51D, DT-40, and DT-20 of Millennium Inorganic Chemicals.

Cellulose is an organic compound with the formula $(C_6H_{10}O_5)_n$, a polysaccharide consisting of a linear chain of β-1,4-linkages, as shown in Scheme I, where n=50 to 20,000. Cellulose is the structural component of the primary cell wall of green plants. Cellulose can be converted into many derivatives.

Scheme I

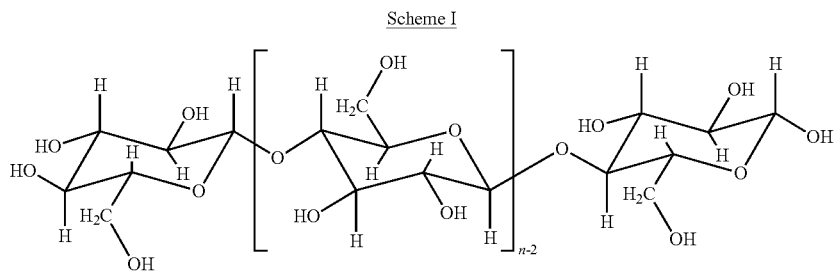

The method uses a carboxyalkyl cellulose. A carboxyalkyl cellulose is a cellulose derivative with carboxyalkyl groups bound to some of the hydroxyl groups of the glucopyranose monomers that make up the cellulose backbone, as shown in Scheme II, where R=H, carboxylalkyl, and m=50 to 20,000. It is often used as its sodium salt, sodium carboxyalkyl cellulose. The functional properties of carboxyalkyl celluloses depend on the degree of substitution of the cellulose structure (i.e., how many of the hydroxyl groups are substituted), as well as the chain length of the cellulose backbone and the degree of clustering of the substituents. The average number of substituted hydroxyl groups per glucose unit in cellulose derivatives is referred to as the degree of substitution (DS). Complete substitution would provide a DS of 3. Preferably, a carboxymethyl celluloses is used. Preferred carboxymethyl celluloses have a degree of substitution of 0.5 to 0.9 (D. B. Braun and M. R. Rosen, *Rheology Modifiers Handbook: Practical Use and Applications* (2000) William Andrew Publishing, pp. 109-131). Carboxymethyl celluloses are known as extrusion aids (U.S. Pat. Nos. 5,884,138 and 6,709,570; U.S. Pat. Appl. Pub. No. 2008/0146721).

Scheme II

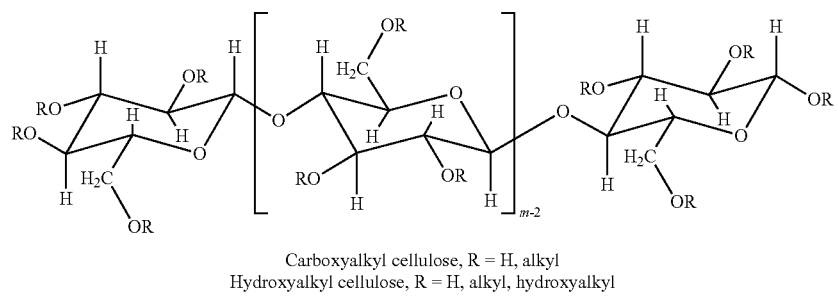

Carboxyalkyl cellulose, R = H, alkyl
Hydroxyalkyl cellulose, R = H, alkyl, hydroxyalkyl The method also uses a hydroxyalkyl cellulose. A hydroxyalkyl cellulose is a derivative of cellulose in which some of the hydroxyl groups in the repeating glucose units are hydroxyalkylated. Some of the hydroxyl groups in a hydroxyalkyl cellulose may also be alkylated. A typical structure of a hydroxyalkyl cellulose is shown in Scheme III, where R=H, alkyl, hydroxyalkyl, and m=50 to 20,000.

Preferably the hydroxyalkyl group is selected from the group consisting of 2-hydroxyethyl, 2-hydroxypropyl, and mixtures thereof. More preferably the hydroxyalkyl cellulose is alkylated. Most preferably, the hydroxyalkyl cellulose is selected from the group consisting of methyl 2-hydroxyethyl cellulose, methyl 2-hydroxypropyl cellulose, and mixtures thereof. Preferably, the degree of methyl substitution is from 1 to 2, more preferably from 1.5 to 1.8; and the 2-hydroxyethyl or 2-hydroxypropyl molar substitution is from 0.1 to 0.3. METHOCEL™ K4M cellulose derivative, a product of Dow Chemical Company and having a methyl substitution of 1.4 and a hydroxypropyl molar substitution of 0.21, is preferably used. Hydroxyalkyl celluloses are known as extrusion aids (U.S. Pat. Nos. 5,884,138, 6,316,383, and 6,709,570).

The weight ratio of the carboxyalkyl cellulose to the titania is preferably from 0.2:100 to 5:100, more preferably from 0.5:100 to 4:100, most preferably from 1:100 to 3:100. The weight ratio of the hydroxyalkyl cellulose to the titania is preferably from 0.1:100 to 2.5:100, more preferably from 0.2:100 to 2:100, most preferably from 0.5:100 to 1:100. The weight ratio of the carboxyalkyl cellulose to the hydroxyalkyl cellulose is preferably from 5:1 to 1:2, more preferably from 3:1 to 1:1.

The method comprises mixing titania, the carboxyalkyl cellulose, and the hydroxyalkyl cellulose to form a dough. If necessary, a solvent may be used. Suitable solvents include water, alcohols, ethers, esters, amides, aromatic compounds, halogenated compounds, and the like, and mixtures thereof. Preferred solvents are water and alcohols.

A titania sol may be used as a source of the titania. A titania sol is a colloidal suspension of titania particles in a liquid. A titania sol can be prepared by hydrolyzing a titania precursor. Suitable titania precursors include titanium salts, titanium halides, titanium alkoxides, titanium oxyhalides, and the like.

The method comprises extruding the dough to produce an extrudate by an operation called extrusion. Extrusion is a process in which a dough is pushed through a die or an orifice to create long objects of a fixed cross-section. Extrusion is commonly used to process plastics or food, and to form adsorbents, catalysts, or catalyst carriers. Any conventional extruder may be used. A suitable screw-type extruder is described in "Particle Size Enlargement," *Handbook of Powder Technology*, vol. 1 (1980) pp. 112-22.

The carboxyalkyl cellulose and the hydroxyalkyl cellulose are used as extrusion aids. An extrusion aid helps the mixing, mulling, and extruding operation and may improve the mechanical and/or physical properties of the extrudate such as crushing strength, surface area, pore size, or pore volume. The extrudate comprising titania, the carboxyalkyl cellulose and the hydroxyalkyl cellulose has a smooth outer surface. They do not tend to stick to each other while being formed, dried, and calcined, which is suitable for large scale production. In addition the combination of the carboxyalkyl cellulose and the hydroxyalkyl cellulose minimizes "feathering." The term "feathering" means that an extrudate, instead of having a smooth outer surface, exhibits cracks in its surface where small flakes or "feathers" of the extrudate are separated from the surface. "Feathering" not only causes loss of valuable material but also tends to impair the physical strength of an extrudate.

Other extrusion aids may be used to form the dough. Other suitable extrusion aids include alkyl amines, carboxylic acids, alkyl ammonium compounds, amino alcohols, starch, polyacrylates, polymethacrylates, poly(vinyl alcohol)s, poly(vinylpyrrolidone)s, poly(amino acid)s, polyethers, poly(tetrahydrofuran)s, metal carboxylates, and the like, and mixtures thereof. Preferred poly(alkylene oxide)s are poly(ethylene oxide)s, poly(propylene oxide)s, or copolymers of ethylene oxide and propylene oxide. Organic extrusion aids are usually removed by calcination.

The extrudate is optionally dried after it is formed. The drying operation removes at least a portion of the solvents from the extrudate. The drying operation may be performed at 30 to 200° C. at atmospheric pressure or under vacuum. The drying may occur in air or an inert atmosphere. Sometimes, it is preferable to raise the drying temperature slowly so the extrudate will not be cracked or weakened.

The method comprises calcining the extrudate to produce a calcined extrudate. Preferably, the calcination is carried out in an oxygen-containing gas to burn off the organic materials (e.g., residual solvent and extrusion aids) contained in the extrudate. The calcination may be carried out at 400 to 1000° C., more preferably from 450 to 800° C., most preferably from 650 to 750° C. Sometimes, it is beneficial to initially calcine the extrudate in an inert atmosphere (e.g., nitrogen, helium) to thermally decompose the organic compounds contained in the extrudate, and then burn off the organic materials in an oxygen-containing gas. Generally, a calcined extrudate after the calcination contains less than 0.5 wt % carbon. Preferably, it contains less than 0.1 wt % carbon.

The method comprises impregnating the calcined extrudate with a palladium compound and a gold compound to produce an impregnated extrudate. Suitable palladium compounds include palladium chloride, sodium chloropalladate, palladium nitrate, palladium sulfate, the like, and mixtures thereof. Suitable gold compounds include auric chloride, tetrachloroauric acid, sodium tetrachloroaurate, the like, and mixtures thereof.

The impregnated extrudate may comprise from 0.1 wt % to 3 wt % of palladium and from 0.1 wt % to 3 wt % of gold and has a weight ratio of palladium to gold within the range of 5:1 to 1:3. More preferably, the impregnated extrudate comprises 0.5 wt % to 1.5 wt % of palladium and 0.25 wt % to 0.75 wt % of gold.

A fixing agent may preferably be added to the extrudate while it is being impregnated. Fixing agents help to bind the palladium compound and the gold compound to the extrudate. Suitable fixing agents include alkali metal, alkaline earth metal, or ammonium compounds, for example, their hydroxides, carbonates, bicarbonates, metasilicates, and the like, and mixtures thereof.

Any suitable impregnation method can be used to produce the impregnated extrudate. The calcined extrudate may be simultaneously or successively impregnated with the palladium compound, the gold compound, and optionally a fixing agent. Preferably it is impregnated with aqueous solutions although other impregnating solvents may be used.

The impregnated extrudate is preferably washed with water or other solvents to remove any halide (e.g., chloride) from the extrudate.

The method optionally comprises drying the impregnated extrudate. Typically the impregnated extrudate can be dried at 50 to 150° C. at atmospheric pressure or under vacuum, primarily to remove at least a portion of the solvents. The drying may occur in air or an inert gas at atmospheric pressure or under vacuum. Sometimes, it is important to raise the drying temperature slowly to prevent the extrudate from losing its mechanical strength.

The method comprises calcining the impregnated extrudate, preferably after it is dried first, to produce the palladium-gold catalyst. Generally, the calcination of the impregnated extrudate occurs at an elevated temperature in a non-reducing atmosphere. Preferably, the calcination of the impregnated extrudate is carried out at a temperature of 150 to 600° C. Suitable non-reducing gases used for the calcination include inert or oxidizing gases such as helium, nitrogen, argon, neon, oxygen, air, carbon dioxide, the like, and mixtures thereof. Preferably the calcination is carried out in an atmosphere of nitrogen, oxygen, or air, or mixtures thereof.

The palladium-gold catalyst obtained from the calcination step is preferably chemically reduced to generate a reduced palladium-gold catalyst. The reduction is usually performed by contacting the palladium-gold catalyst with a reducing agent. Suitable reducing agents include hydrogen, carbon monoxide, hydrocarbons, olefins, aldehydes, alcohols, hydrazine, the like, and mixtures thereof. Hydrogen, ethylene, propylene, alkaline hydrazine and alkaline formaldehyde are preferred reducing agents and ethylene and hydrogen are particularly preferred. Temperatures employed for the reduction can range from 20 to 700° C. If hydrogen is the reducing agent, a gas mixture containing hydrogen and another gas such as argon, helium, nitrogen, or the like, is usually used. The reduction temperature with hydrogen is preferably in the range of 300 to 700° C., more preferably in the range of 450 to 550° C.

The palladium-gold catalyst prepared according to the invention can be used for the acetoxylation of an olefin, such as ethylene or propylene, to produce an acetoxylated olefin such as vinyl acetate or allyl acetate. Preferably, a promoted palladium-gold catalyst, which can be produced by adding an activator to the reduced palladium-gold catalyst, is used in the acetoxylation reaction. An activator is an alkali or alkaline earth metal compound, examples of which are hydroxides, acetates, nitrates, carbonates, and bicarbonates of potassium, sodium, cesium, magnesium, barium, and the like. Potassium salts are preferred activators. The activator content may be in the range of 0 to 15 wt %, preferably 1.5 to 10 wt % of the catalyst.

The invention also include a process for preparing vinyl acetate, comprising reacting a feed comprising ethylene, oxygen, and acetic acid in the presence of the palladium-gold catalyst, preferably in the presence of the reduced palladium-gold catalyst, more preferably in the presence of the promoted palladium-gold catalyst.

The feed typically comprise 20 to 70 mol % ethylene, 2 to 8 mol % oxygen, and 2 to 20 mol % acetic acid. The feed may comprise a diluent. Examples of suitable diluents include propane, nitrogen, helium, argon, carbon dioxide, the like, and mixtures thereof.

The reaction is generally performed at a temperature in the range of 100 to 250° C., preferably 125 to 200° C. and under a pressure of 15 to 500 psig.

Example 1

D-T51 titania (2500 g), a high-purity WALOCEL™ C sodium carboxymethyl cellulose (The Dow Chemical Company, 52.5 g), poly(ethylene oxide) (MW=100,000, 35 g), and a cellulose derivative (METHOCEL™ K4M, 25 g) are mixed in an Eirich mixer for 5 min. Water (1005 g), an aqueous ammonium hydroxide (14.8 M, 100 g), and benzyl alcohol (17.5 g) are added into the mixer. They are mixed for 5 min at the "low" speed setting, then for 10 min at the "high" speed setting. The dough produced is placed in the hopper of a Bonnot 2-inch extruder (The Bonnot Company) equipped with a die face of 25 holes with a diameter of ⅛ inch. The extrusion is performed at a rate of approximately 0.25 kg/min. The extrudates produced have smooth outer surface and there is minimal sticking each other occurring. Almost no feathering is observed.

The extrudates are piled 1 inch deep on a collection tray and dried in air at 80° C. for 12 h. Then they are calcined in air. The calcination temperature is raised from room temperature to 500° C. at a rate of 2° C./min, held at 500° C. for 2 h, raised from 500° C. to 700° C. at a rate of 10° C./min, held at 700° C. for 3 h, then lowered to room temperature.

Some physical properties of the calcined titania extrudate are listed in Table 1. The crush strength of the calcined titania extrudate is measured with a Chatillon crush strength analyzer (Model DPP 50). The force necessary for failure in 25 measurements is averaged to give the reported value. Bulk density is measured by placing 40 g of the calcined extrudates in a 100-mL graduated cylinder (1" nominal outer diameter). The graduated cylinder is tapped until the apparent volume no longer changes, and then this value is divided into the mass to calculate the bulk density. Voidage is determined by adding the pellets to 50 mL water in a second graduated cylinder and then tapping until all voids are filled. The resulting water level is subtracted from the total volume of the water and the pellets taken separately to determine the void volume occupied by water. Total pore volume is determined by pouring the mixture through a sieve basket, shaking to remove excess water and then weighing the wet extrudates. The increase in mass over the initial 40 g of extrudates divided by the density of water is taken as the measure of the pore volume.

Comparative Example 2

The procedure of Example 1 is repeated with the formulation shown in Table 1. The extrudates are droopy as they exit the die face of the extruder and tend to stick to each other as they lay on the collection tray.

Comparative Example 3

The procedure of Example 1 is repeated with the formulation shown in Table 1. The extrudates are droopy as they exit the die face of the extruder and tend to stick to each other as they lay on the collection tray.

TABLE 1

| Example | 1 | C. 2 | C. 3 |
|---|---|---|---|
| Formulation | | | |
| DT-51 Titania (g) | 2500 | 2500 | 2500 |
| Water (g) | 1005 | 1250 | 1005 |
| Poly(ethylene oxide) (g) | 35 | 35 | 35 |
| WALOCEL ™ C cellulose (g) | 52.5 | 52.5 | 52.5 |
| Benzyl alcohol (g) | 17.5 | 17.5 | 17.5 |
| Ammonium hydroxide (g) | 100 | 100 | 100 |
| METHOCEL ™ K4M cellulose (g) | 25 | 0 | 0 |
| Extrusion Processability | good | poor | poor |
| Properties of Calcined Extrudate | | | |
| Crushing strength (lb/mm) | 1.68 | 1.37 | 1.43 |
| Surface area (m$^2$/g) | 27.2 | n/a | n/a |
| Pore volume (mL/g) | 0.32 | 0.30 | 0.30 |

Comparative Example 4

The procedure of Example 1 is repeated, except that the formulation is as follows: DT-51 (2000 g), TAMOL™ 1124 dispersant (a hydrophilic polyelectrolyte copolymer from The Dow Chemical Company, 32.6 g), METHOCEL™ K4M cellulose derivative (54.6 g), lactic acid (6 g), water (950 g), aqueous ammonium hydroxide (14.8 M, 70 g).

Comparative Example 5

The procedure of Example 4 is repeated, except that alumina (DISPERAL® P2, available from Sasol, 20 g) is used. The extrudates are droopy as they exit the die face of the extruder and tend to stick to each other as they lay on a metal tray. The calcined extrudate contains 1 wt % alumina and 99 wt % titania.

TABLE 2

| Example | C. 4 | C. 5 |
|---|---|---|
| Formulation | | |
| DT-51 titania (g) | 2000 | 2000 |
| METHOCEL ™ K4M cellulose (g) | 54.6 | 54.6 |
| TAMOL ™ 1124 dispersant (g) | 32.6 | 32.6 |
| Water (g) | 950 | 950 |
| Ammonium hydroxide solution (g) | 70 | 70 |
| DISPERAL ® P2 alumina (g) | 0 | 20 |
| Lactic acid (g) | 60 | 60 |
| Extrusion Processability | poor | poor |

Example 6

The procedure of Example 1 is repeated, except that the formulation is as follows: DT51 (300 g), TAMOL™ 1124 dispersant (5 g), WALOCEL™ C cellulose (6 g), METHOCEL™ K4M cellulose derivative (6 g), lactic acid (4.5 g), water (155 g), and aqueous ammonium hydroxide (14.8 M, 11 g). The extrudates have smooth outer surface. Minimal feathering is observed. Almost no extrudate is observed to stick to others.

Comparative Example 7

The procedure of Example 6 is repeated, except that the formulation is shown in Table 3. The extrudates slump upon exiting the die. They stick to each other on the collection tray.

Comparative Example 8

The procedure of Example 6 is repeated, except that the formulation is shown in Table 3. The extrudates do not tend to stick to each other after laying the on the collection tray. However, they appear to be feathering.

TABLE 3

| Example | 6 | C. 7 | C. 8 |
|---|---|---|---|
| Formulation | | | |
| DT-51 titania (g) | 300 | 300 | 300 |
| Water (g) | 155 | 145 | 145 |
| TAMOL ™ 1124 dispersant (g) | 5 | 5 | 5 |
| WALOCEL ™ C cellulose (g) | 6 | 0 | 6 |
| Lactic acid (g) | 4.5 | 4.5 | 4.5 |
| Ammonium hydroxide (g) | 11 | 11 | 11 |
| METHOCEL ™ K4M cellulose (g) | 6 | 6 | 0 |
| Extrusion Processability | good | poor | poor |

Example 9

NaHCO$_3$ powder (27 g) is slowly added to an aqueous solution containing Na$_2$PdCl$_4$.3H$_2$O (31.4 g), NaAuCl$_4$.2H$_2$O (11.3 g), and water (235.4 g). The mixture is stirred at room temperature for 10 min. The solution is sprayed with a pipette on calcined titania extrudates prepared in Example 1 (1000 g) while they are being tumbled in a rotating flask. Once the impregnation is finished, the rotating flask is heated to about 100° C. with a heat gun. The impregnated extrudates are tumbled for another 30 min at 100° C., then placed in an oven at 80° C. for 2 h before they are cooled to room temperature.

The dried extrudates are washed with warm water (50-80° C.) until no chloride can be detected by mixing the wash filtrate solution with a 1 wt % silver nitrate solution to observe precipitation. After washing is finished, the catalyst is dried at 80 to 100° C. to remove water. Then they are heated at 230° C. for 3 h in air, and at 230° C. for 30 min under a nitrogen flow. The temperature is raised to 500° C. under a flow of 10 mol % hydrogen in nitrogen gas, and held for 3 h before it is cooled to room temperature.

The extrudates are washed with an aqueous solution containing 10 wt % potassium acetate and 1 wt % potassium hydroxide (10 L). The washed extrudates are dried under nitrogen at 125° C. for 2 h. A palladium-gold catalyst is obtained. It contains 0.93 wt % Pd, 0.54 wt % Au, and 1.5 wt % K.

Example 10

The palladium-gold catalyst prepared in Example 9 is tested for vinyl acetate production in a fixed-bed reactor (stainless steel, 1 inch O.D.). The reactor is charged with a mixture of the catalyst (10 g) and an inert alpha alumina cylindrical pellets (⅛" in diameter, surface area 4 m$^2$/g, pore volume 0.25 mL/g, 25 g). The feed contains 46.1 mol % helium, 33.9 mol % ethylene, 11.48 mol % acetic acid, 4.2 mol % oxygen, and 4.2 mol % nitrogen. The reactor pressure is 80 psig and the space velocity relative to the volume of the catalyst is 3050 $h^{-1}$ at standard temperature and pressure. The reactor is cooled using a fluidized sand bath, the to temperature of which is set at 130° C. The product stream is analyzed by gas chromatography (GC). Oxygen conversion, oxygen selectivity, oxygen yield to vinyl acetate, and ethylene selectivity to vinyl acetate between 75 to 100 h on stream are calculated from the GC results and listed in Table 4. Oxygen conversion is calculated by dividing the amount of oxygen consumed by the total amount of oxygen fed to the reactor. Oxygen selectivity to vinyl acetate is the amount of oxygen consumed in making vinyl acetate divided by the total amount of oxygen consumed. Oxygen yield to vinyl acetate is the product of oxygen conversion multiplied by oxygen selectivity. Ethylene selectivity to vinyl acetate is the amount of ethylene consumed in making vinyl acetate divided by the total amount of ethylene consumed. Catalyst productivity is the grams of vinyl acetate produced per liter of the catalyst per hour.

TABLE 4

| | |
|---|---|
| Oxygen conversion (%) | 63.7 |
| Oxygen selectivity to vinyl acetate (%) | 86.3 |
| Oxygen yield to vinyl acetate (%) | 54.9 |
| Ethylene selectivity to vinyl acetate (%) | 97.4 |
| Catalyst productivity (g · $L^{-1}$ · $h^{-1}$) | 492.2 |

I claim:

1. A process for preparing vinyl acetate, comprising the steps of:
   (i) preparing a palladium-gold catalyst, wherein the preparing step further comprises the steps of:
      (a) mixing titania, a carboxyalkyl cellulose, and a hydroxyalkyl cellulose to form a dough;
      (b) extruding the dough to produce an extrudate;
      (c) calcining the extrudate to produce a calcined extrudate;
      (d) impregnating the calcined extrudate with a palladium compound and a gold compound to produce an impregnated extrudate; and,
      (e) calcining the impregnated extrudate to produce the palladium-gold catalyst
   (ii) reacting ethylene, oxygen, and acetic acid in the presence of the palladium-gold catalyst.

2. The process of claim 1 wherein the palladium-gold catalyst is further reduced.

3. The process of claim 2 wherein the palladium-gold catalyst is reduced by hydrogen.

4. The process of claim 3 wherein the reduced catalyst is further promoted by an activator.

5. The process of claim 1 wherein the titania is anatase.

* * * * *